United States Patent [19]

Lindmo

[11] Patent Number: 5,585,241
[45] Date of Patent: Dec. 17, 1996

[54] METHOD OF ASSAY

[75] Inventor: Tore Lindmo, Kolbotn, Norway

[73] Assignee: Sinvent A/S, Norway

[21] Appl. No.: 457,158

[22] Filed: Jun. 1, 1995

Related U.S. Application Data

[63] Continuation of Ser. No. 924,397, Aug. 3, 1992, abandoned, which is a continuation of Ser. No. 602,269, filed as PCT/GB89/00506, May 10, 1989, abandoned.

[30] Foreign Application Priority Data

May 11, 1988 [NO] Norway ................................ 88 2067

[51] Int. Cl.$^6$ ................................................ C12Q 1/68
[52] U.S. Cl. ........................... 435/6; 435/808; 435/810; 435/962; 436/523; 436/172; 436/533; 436/534; 436/517; 436/800; 436/805
[58] Field of Search ........................ 435/6, 7, 21, 810, 435/962, 808; 436/523, 546, 172, 175, 533, 534, 517, 800, 805

[56] References Cited

U.S. PATENT DOCUMENTS

| | | | |
|---|---|---|---|
| 4,556,642 | 12/1985 | Collet-Cassart et al. | 436/500 |
| 4,590,169 | 5/1986 | Cragle et al. | |
| 4,595,661 | 6/1986 | Cragle et al. | 436/534 |
| 4,665,020 | 5/1987 | Saunders et al. | 435/7 |
| 4,680,274 | 7/1987 | Sakai et al. | 436/512 |
| 5,047,321 | 9/1991 | Loken et al. | 435/6 |

FOREIGN PATENT DOCUMENTS

| | | |
|---|---|---|
| 0163312 | 4/1985 | European Pat. Off. |
| 8502258 | 5/1985 | WIPO |

OTHER PUBLICATIONS

Saunders, G. Amplified Flow–Cytometric Separation—Free Fluorescence Immunoassays, 1985, 2020–2023.

*Primary Examiner*—James C. Housel
*Assistant Examiner*—Bao-Thuy L. Nguyen
*Attorney, Agent, or Firm*—Bacon & Thomas

[57] ABSTRACT

A method for the flow cytometric assay of an analyte using monodisperse particles carrying a specific binding partner, the analyte and binding partner being selected from the group consisting of (a) antigen and specific antibody, (b) hormone and hormone receptor, (c) hapten and antihapten, (d) polynucleotide and polynucleotide binding protein, (e) biotin and avidin or streptavidin, (f) enzyme and enzyme cofactor and (g) lectin and specific carbohydrate, and the method comprising the steps of adding to the aqueous sample a predetermined amount of particles and a predeterminded amount of a labelled ligand having affinity for the analyte or the binding partner and detecting and quantifying the resulting labelled ligand-carrying particles by a flow cytometer, the method using a pair of different particle types which are distinguishable from each other by the flow cytometer and which respectively carry binding partners having the same specificity but different binding affinity for the analyte and independently but simultaneously detecting the two types of labelled ligand-carrying particles by the flow cytometer.

10 Claims, 6 Drawing Sheets

FIG. 3A  FIG. 3B
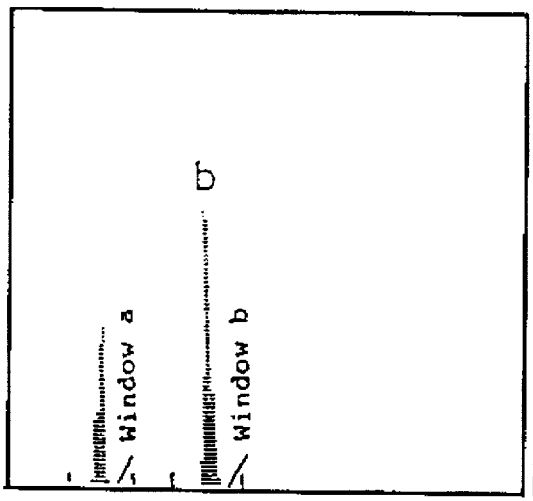
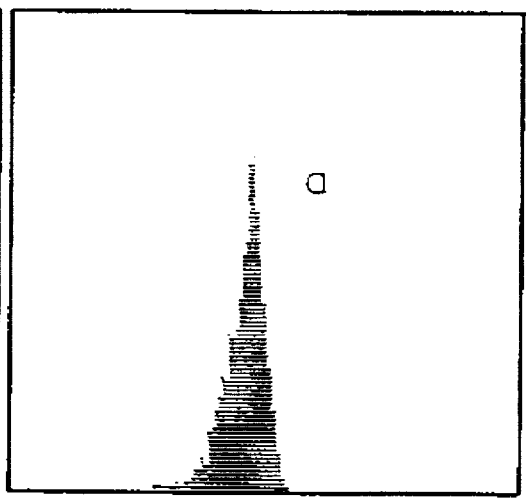
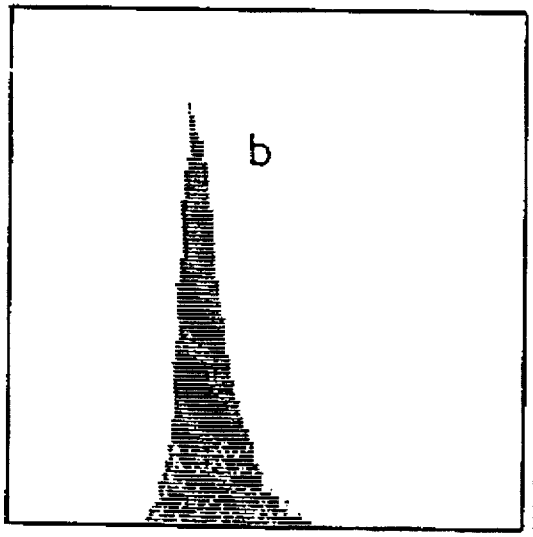
FIG. 3C  FIG. 3D

FIG. 4A
FIG. 4B
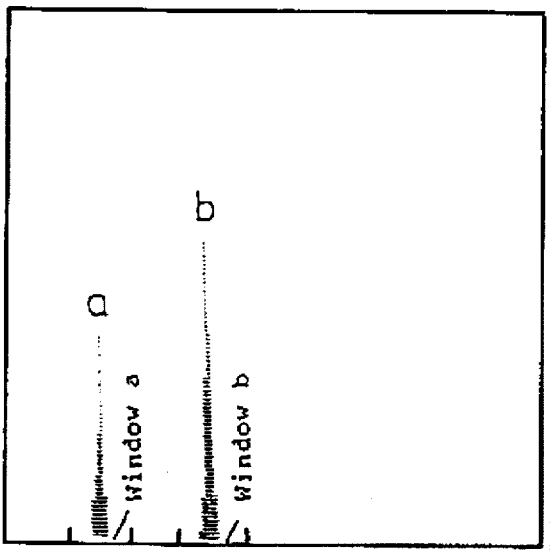
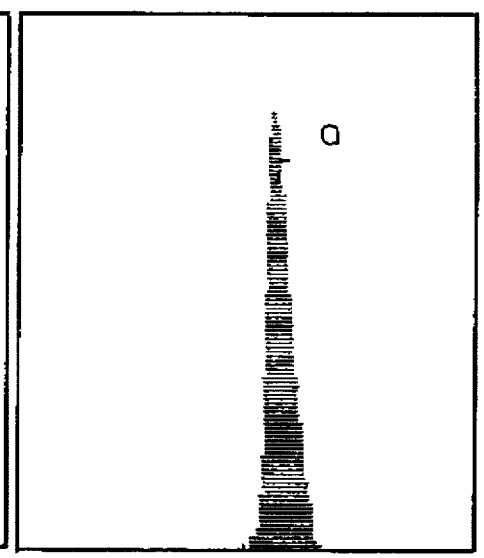
FIG. 4C
FIG. 4D
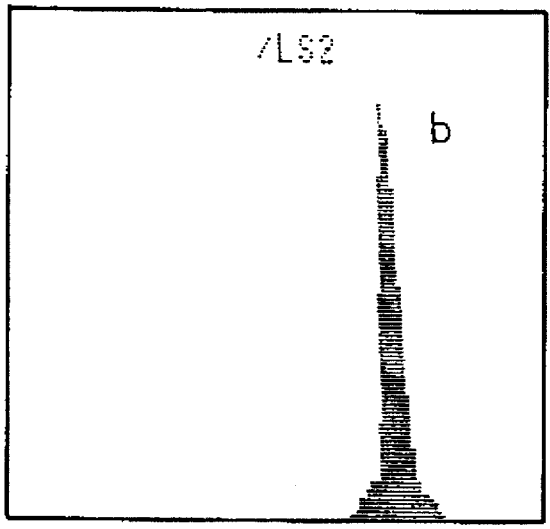
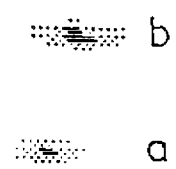

METHOD OF ASSAY

This application is a continuation of application Ser. No. 07/924,397, filed Aug. 3, 1992, now abandoned, which is a continuation of application Ser. No. 07/602,269, Dec. 10, 1990, now abandoned.

The present invention concerns a method of assay, in particular a method of immunoassay.

Immunological and related techniques are important assay methods in clinical laboratories for determination of constituents such as antigens in serum samples. Such substances often are found in low concentrations i.e. nmol/l to pmol/l, and even lower for some antigens. The methods are commonly based on the use of a binding partner having specificity for the analyte to be assayed, this binding partner often being coupled to a solid phase e.g. the plastic surface of a reaction well or the surfaces of plastic particles.

One class of such methods (competitive binding radio-immuno-assays) utilizes a radioactively labelled molecule identical to the antigen or other analyte to be determined. Thus for example, addition of a known amount of radiolabelled antigen in the presence of a small amount of a binding partner, will lead to competitive binding of the radiolabelled and the naturally occurring antigen in the sample, and this permits a determination of the concentration of the antigen by means of a previously established standard curve.

Another class of such methods (sandwich assays) utilizes a larger amount of binding partner. This binds the analyte of the sample, and the amount of bound analyte is indicated by addition of a secondary indicator binding partner which binds to the antigen, the latter being labelled for reading, for example on the basis of radioactivity, light absorption or fluorescence. This class of methods often has greater sensitivity than competitive binding assays and is therefore usually to be preferred.

Common to all these methods is that excess of unbound labelled component must be washed off prior to reading. Therefore it is convenient to have the primary binding partner coupled to a solid phase, in order to facilitate the washing-off of free labelled component.

A common way of implementing such an assay is to prepare a micro-titre plate of 96 (8×12) 400 ul wells by coupling the binding partner to the surface of the wells. During incubation after addition of the sample, the analyte will be bound to the surface of the well by the binding partner. The labelled component is subsequently added and binds to the analyte. After the plate has been washed to remove free labelled component, the plate can be read for example photometrically if the label provides a visual signal.

It is known that by coupling the binding partner to the surface of microscopic particles, it is possible to obtain a large total surface coated with the binding partner. Particles are also suitable as a solid phase from the point of view of separating bound from free reactants, since they can easily be immobilized e.g. on a filter where the washing buffer is let through. A different approach is to use iron-containing particles which can be immobilized on the vessel wall by means of an externally applied magnet, while excess reagents are rinsed off.

In the above-mentioned methods, the separation step represents a significant part of the labour cost.

It is, however, known that particle-based immunometric assays can be read by flow cytometry without necessarily having to remove unbound indicator prior to measurement. Flow cytometry is a method of assaying particles in fluid suspension; the particles may be of any type and are not limited to cells. Norwegian patents Nos. 144002 and 145176 show a typical method whereby single particles in suspension are passed though the measurement region of a photometer wherein the excitation light causes the emission of a pulse of scattered light related to particle size, and a further signal, e.g. a pulse of fluorescence light related to the particle-associated amount of bound label. Suitable electronic detectors and microprocessor electronics classify and store the results for each particle coming through. Thus, a measurement result from 10,000 to 100,000 individual particles is easily obtained in one minute of data acquisition time. A characteristic feature of flow cytometry is the principle of hydrodynamic focussing of the sample stream. This creates a measurement region (volume of sample stream inside the excitation/+detection region) of the order of 10 $\mu m^3$. The amount of unbound indicator present in the liquid surrounding the particle in the measurement region will therefore be too small to significantly influence the measurement. Thus, reading of particle-based assays can be performed by flow cytometry without having to separate free from bound reagents prior to reading. Such an assay is said to be homogeneous, i.e. separation-free.

One problem concerning the use of flow cytometry as a reading device relates to the sensitivity and dynamic range of the method. High sensitivity dictates the use of a small number of binding particles in order to have a reasonable amount of bound analyte (and thus label) per particle, even at low concentrations of the analyte in the sample. This is due to the fact that measurement accuracy in the flow cytometer is related to intensity per particle of the signal from the label. In order to be able to measure high concentrations of analyte, it is desirable to use a large number of binding particles. Since each particle has a certain number of binding sites for the analyte, the sum of all particles will represent a certain binding capacity, and this defines the upper limit for the highest measurable concentration of analyte. Since the amount of labelled compound is assumed constant, the amount of label per analyte molecule will decrease as the amount of analyte increases beyond maximum capacity. At analyte concentrations higher than the saturating concentration the amount of label bound per particle will therefore decrease since an increasing amount of the available label will be bound to the excess of free analyte in the solution. This is a well-known phenomenon, the Hook-effect.

It will be known to the expert that the abovementioned Hook-effect may be prevented by increasing the amount of binding partner in the assay to enable binding of larger amounts of analyte before saturation occurs. In particle-based assays this means a high binding capacity per particle and an increase in the number of particles relative to the amount of analyte to be determined. An increase in the number of particles will, however, lead to less binding per particle at a certain analyte concentration in the sample. Such an approach will therefore give lower sensitivity, i.e. result in a higher limit for the lowest detectable concentration of analyte.

The present invention combats the above problems and permits exploitation of the advantages of flow cytometric reading in that separation of free and bound reagents is not required. The present invention makes it possible to obtain high sensitivity and at the same time increase the valid measurement range of the method. In addition to the advantages the present method gives in terms of high sensitivity and increased measurement range, it will also give improved measurement precision.

In assays of the kind here concerned it is necessary to establish a standard curve which quantitatively shows the measured amount of label bound to the coated solid phase, as a function of analyte concentration of the sample (usually depicted on a logarithmic scale). It is known that the dominating factor in determining the position (left-right) of the standard curve in relation to the dose axis showing analyte concentration in the sample, is the affinity of the binding partner for the analyte. U.S. Pat. No. 4595 661 utilizes this fact in an immunoassay where in addition to the principal antibody is added another antibody of lower binding affinity for the analyte. This antibody may be coupled to a solid phase or be labelled. The patent is based on the measurement of the sum of the contributions from the two binding reactions taking place in such a mixed system, where the antibody of low affinity will make a significant contribution only at high ligand concentrations and thus forestall the Hook-effect. The reason for this is that the standard curve for the low affinity antibody alone is shifted to the right (higher dose) compared to the standard curve of the ordinary antibody.

It has new been found that if the high and low affinity analyte binding partners are coated separately onto particles of different types which can be distinguished in flow cytometry, the amounts of analyte bound by the high-affinity and by the low-affinity binding partners can be independently, but simultaneously measured in the same sample by flow cytometry after incubation with the binary mixture of particles. Thereby, the principal aim is achieved, namely to avoid the Hook-effect. Furthermore compared to other known methods the method of the invention has the following advantages:

1) The sensitivity i.e. lowest detectable analyte concentration, which is mainly determined by the high-affinity binding partner and the degree of non-specific binding, will not be reduced by addition of low-affinity particles when both binding parameters are measured, in contrast to a system where only the total sum of the two contributions to the binding is measured, as in U.S. Pat. No. 4595 661.

2) The method of the invention uses a double standard curve, one from each particle type. Each sample measurement therefore results in two measurement values, and the two values must fit as a pair to the double standard curve for the analyte concentration in question. This provides additional reliability in the assay, since a pair of values that do not fit indicates deviation from normal assay performance.

3) In order to utilize the dynamic range of the detector, it is an advantage to use smaller particles for the high-affinity antibody and larger particles for the antibody of lower affinity. Thereby the maximum measurement values for each particle type will be of comparable magnitude, and thus utilize the detector optimally.

U.S. Pat. No. 4743 542 discloses a more trivial approach to avoiding the Hook-effect at high analyte concentrations. The principle is merely to add unlabelled antibody in competition with labelled antibody. This corresponds to using a larger amount of antibody of lower specific labelling; an increased capacity is therefore obtained in the assay and the onset of the Hook-effect will be shifted to higher analyte concentrations. Unlabelled antibody is used as the additional reagent in order to avoid increasing the measurement values beyond the detector range at high analyte concentrations, and this also keeps the level of non-specific binding at the original level. What is obtained is therefore a less steep standard curve which covers a wider range of analyte concentrations. However, the reduced slope of the curve results in larger uncertainty in the analyte concentration in an unknown sample. Therefore the end result may be an only insignificant increase in the effective dynamic range of the assay whereas the method of the invention gives an increased dynamic range without impairment of measurement sensitivity or precision.

According to the present invention, there is provided a method of assay of one or more analytes in an aqueous sample wherein for each analyte to be assayed monodisperse particles carrying a specific binding partner for that analyte are used to bind the said analyte and a labelled ligand is used to indicate the amount of said bound analyte, the amount of labelled ligand bound to the particles being determined by a flow cytometer, characterised in that for each analyte to be assayed a pair of different particle types is used the particles of each of the two particle types of said pair carrying a binding partner having the same specificity but having a different binding affinity for the said analyte, the pair of particle types which has reacted with each analyte to be assayed and become labelled by a labelled ligand being distinguishable by the flow cytometer from each other and from the pairs of particle types which have reacted with each other analyte to be assayed.

In general, the particle types used in the method of the invention may be distinguished on the basis of size. Conventional flow cytometers can use light scattering to detect each particle and the light scattering signal is proportional to particle size so that particles of different sizes can be readily distinguished, providing the size-ranges of the respective populations do not overlap. Particle size can also be determined by the Coulter principle based on the change in electrical impedance due to each particle. The Coulter principle can also be used to distinguish particles of identical or overlapping size ranges but having different impedance characteristics.

Where more than one analyte is to be assayed pairs of particle types will be used such that the signals from all particle types can be distinguished. If the label used is the same for each analyte in the sample to be assayed, the pairs of particle types for the respective analyte will have to be distinguishable from other malts of particle types on the basis of the characteristics of the particles, e.g. size. The Dynosphere™ particles available today are perfect spheres with a relative standard deviation (CV) in light scatter measurements of about 1%. A number of such particle types can therefore be mixed and still easily identified as non-overlapping populations in a flow cytometric light scatter histogram. Uniformity in size and surface properties are also important for the analyte binding properties of the particles. This results in less variance in immunofluorescence or other signals between particles of the same type, and thereby gives more precisely defined histograms and mean values.

If, however, different labels are used for each analyte, the pairs of particle types may be the same for each analyte and qualitative differences in the signals from the labels e.g. fluorescence wavelength, will distinguish the respective particle populations.

The preferred labels for use in the method of the invention are fluorescent substances commonly used in fluorometric flow cytometry e.g. fluorescein or phycoerythrin. Fluorescently stained microspheres (0.10 micrometers diameter) may also be used as the label (Saunders et al Clin. Chem. 31,2020). Other labels providing a photometric signal include colloidal gold particles. Labels providing significant differences in electrical impedance, for example metal particles such as gold, may also be used to provide a signal which may be detected by the Coulter principle while differences in particle type may be determined by, for example, light scattering.

The method of the invention may be used to assay a wide range of analytes, using particles carrying suitable specific binding partners. Analyte and binding partner pairs which may be concerned include the following (it will be appreciated that in such reactive pairs, either member may be the analyte):

(a) antigen and specific antibody (b) hormone and hormone receptor (c) hapten and antihapten (d) polynucleotide and complementary polynucleotide (e) polynucleotide and polynucleotide binding protein, (f) biotin and avidin or streptavidin (g) enzyme and enzyme cofactor and (h) lectin and specific carbohydrate.

The members of the above pairs may also be attached to other molecules to be assayed. Thus, for example, biotin or a hapten may be covalently attached to the analyte in a preliminary step prior to the assay.

The preferred analytes for assay according to the invention are antigens and the preferred binding partners are monoclonal antibodies.

The method of the invention may be applied primarily to sandwich assays and variations of these. Thus, in a sandwich assay, the analyte may bind to the particles and the labelled ligand will be a binding partner which simply binds to the analyte before or after reaction with the particles to provide signal proportional to the amount of analyte. The labelled ligand may be added to the sample before or after the particles or simultaneously therewith.

According to a further feature of the invention there is also provided a kit for use in the flow cytometric assay of one or more analytes in a sample comprising:

(a) for each analyte to be assayed, monodisperse particles carrying a first specific binding partner for that analyte;

(b) for each analyte to be assayed, monodisperse particles carrying a second specific binding partner having the same specificity as said first specific binding partner but a different binding affinity for the analyte;

(c) a labelled ligand or ligands serving to indicate the amount of each bound analyte; the monodisperse particles (a) and (b) being distinguishable from each other and from any particle types corresponding to other analytes in the sample such that all particle types used can be separately determined by the flow cytometer after reaction with the respective analytes and becoming labelled by said labelled ligand.

The improvement in dynamic range obtained by the present binary assay will largely depend upon the difference in association constant between the two binding partners used to coat the pair of particle types. The larger the difference, the larger the separation between the two standard curves. In general, a 5–100 fold difference in association constant is appropriate.

The increased dynamic range of the present binary assay is obtained without compromising the high sensitivity provided by the high affinity particles. Further increase in sensitivity may be obtained by washing the particles prior to analysis in cases where nonspecific binding is significant, although the advantage of a separation-free assay then would be lost.

Recently, the importance of estimating sample specific variations in non-specific binding has been pointed out for conventional ELISA in microtitre plates; for each sample nonspecific binding was individually determined by the binding observed in a well coated with an irrelevant antibody. This approach can be incorporated into the particle based flow cytometric assay by introducing another distinguishable particle type, coated with an irrelevant antibody, i.e. one having zero affinity for any analyte to be assayed. This could be a third particle size added to the binary mixture described above. An important advantage over conventional assays is that all determinations are done on a single sample.

Simultaneous determinations of analyte binding to two or more different particle types by flow cytometry results in increased reliability of the assay compared to single measurements based for example on radioactivity counting. Firstly, the particle type related histogram of the sample is expected to remain unchanged throughout the series of samples identically set up. This would confirm the reliability of the flow cytometric analysis. Secondly, determining the analyte concentration of the sample from two measures, for example the mean fluorescence intensities of the two types of particles referred to the double standard curve, could reveal deviation from normal performance of the assay if the two measures as a pair did not fit well to the double standard curve for any concentration.

The invention is further illustrated with reference to the following figures:

FIG. 3 and 4 show examples of measurements made by the flow cytometer.

Figure 5:
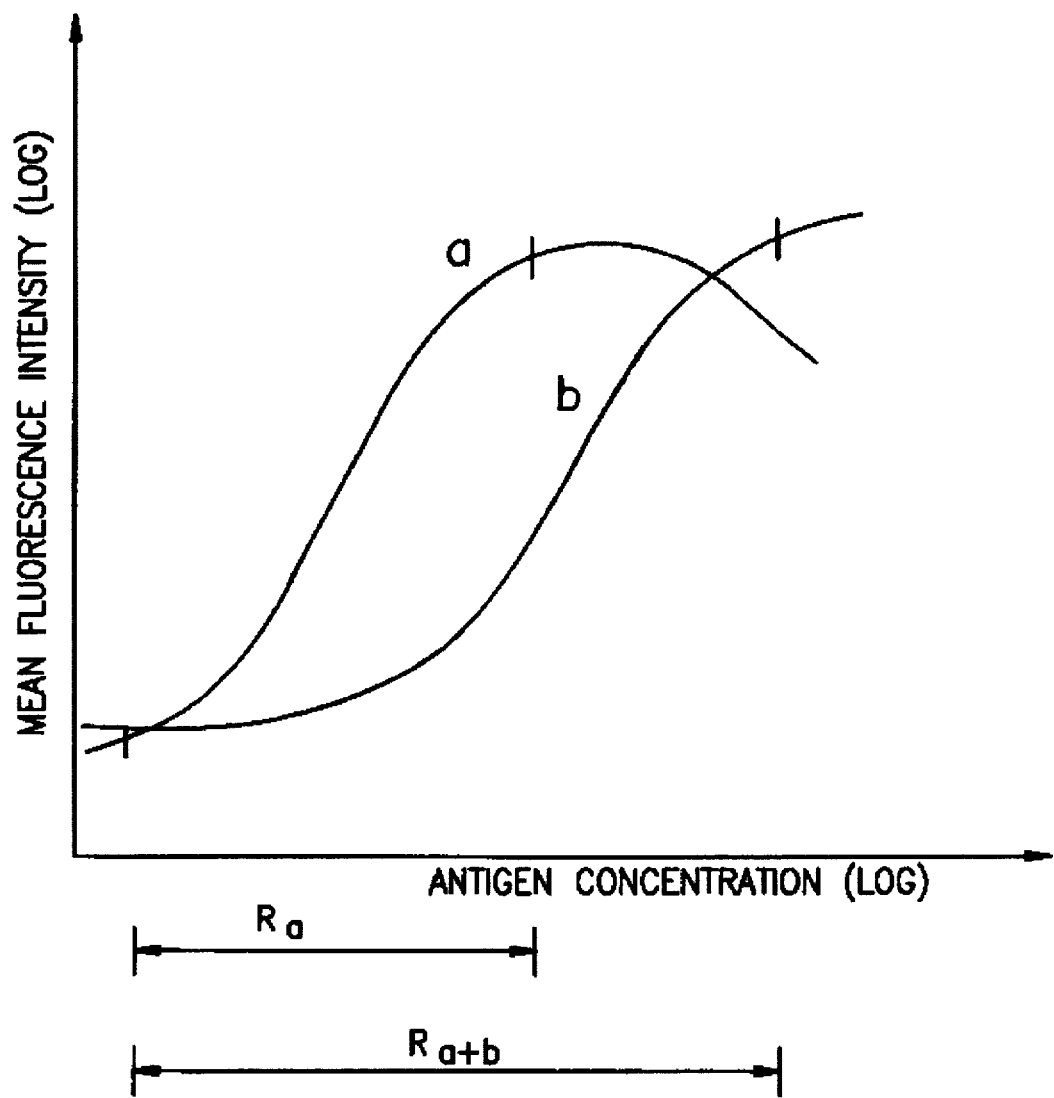
Figure 6A:
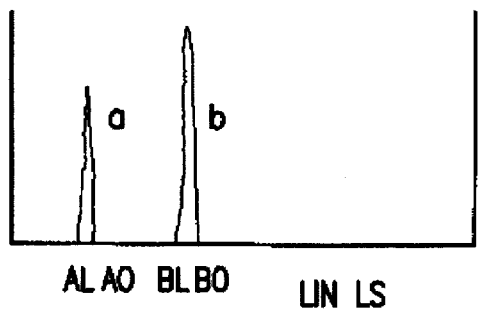
Figure 6C:
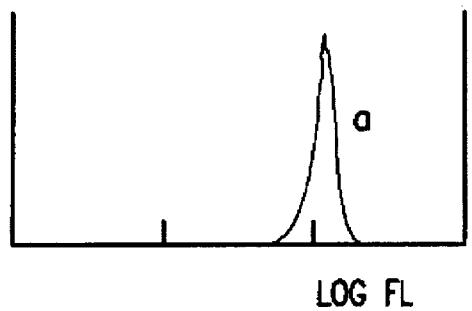
Figure 6B:
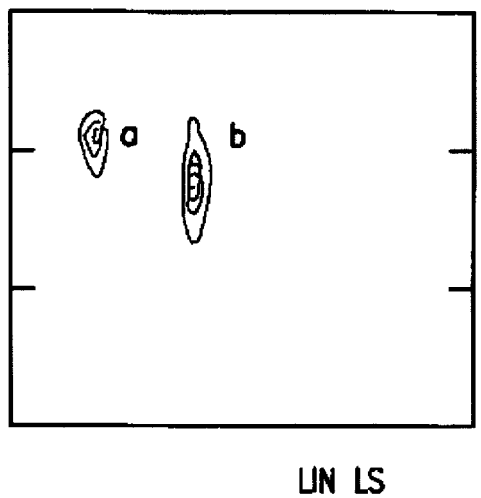
Figure 6D:
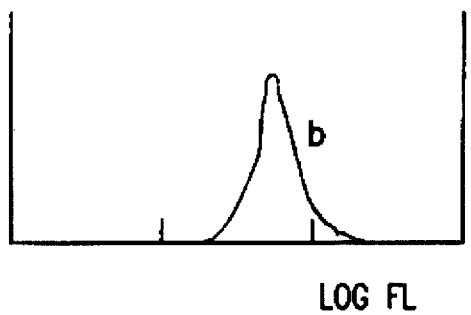

FIG. 5 gives an illustration of the double standard curve which is used in the method according to the invention.

FIG. 6 shows the histograms obtained in accordance with the Example hereinafter.

FIG. 7 shows the double standard curve and precision profile for the results from the Example hereinafter.

Particle 1 (of type a) is coated with a certain binding protein 2 (monoclonal antibody) directed against a binding site (epitope) on the antigen to be measured. This binding protein is chosen to have a very high binding affinity (association constant) for the antigen. Particle 3 (of type b) is different from particle 1 (type a) in such a way that the two particle types can be identified in the flow cytometer independently from the fluorescence measurement. This is easily achieved by using particle types of different size which give rise to light scatter signals of different intensity. Particle volume measurement based on the Coulter principle (measurement of a change in electrical impedance in the orifice due to the passing particle), which also is available in some flow cytometers, is also suitable for identification of the two particle types. Particles of type b are coated with a binding protein 4 (monoclonal antibody) with specificity for the same binding site on the antigen as binding protein 2, but the former has a lower association constant than the latter. In addition to certain fixed amounts of the particles a and b, the test reagent contains a certain amount of labelled antibody 5. This antibody is preferentially directed against a binding site different from the one binding antibodies 2 and 4. It is furthermore convenient if there exists only one of each of the two binding sites per antigen molecule, since this will prevent aggregation of the particles.

Figure 1:
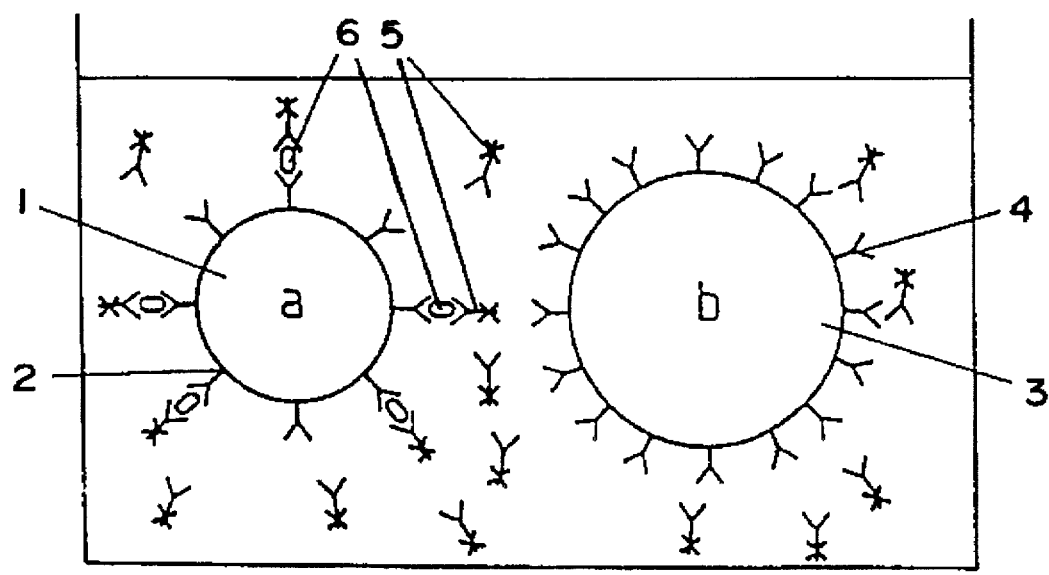
FIG. 1 depicts the binding reaction for the two types of particles in the presence of a low concentration of antigen.

When antigen 6 is present in a low concentration in the sample (FIG. 1), the antigen will preferentially bind to the high affinity binding sites on particles of type a. Particles of type b will therefore bind an insignificant amount of antigen under these conditions. By secondary binding of the indicator antibody, particles of type a will therefore be detected with a certain fluorescence, while particles of type b will have insignificant fluorescence under these conditions. Since particles of type a are present in a relatively low concentration, even small amount of antigen will lead to detectable particle-associated fluorescence, i.e. high measurement sensitivity.

Figure 2:
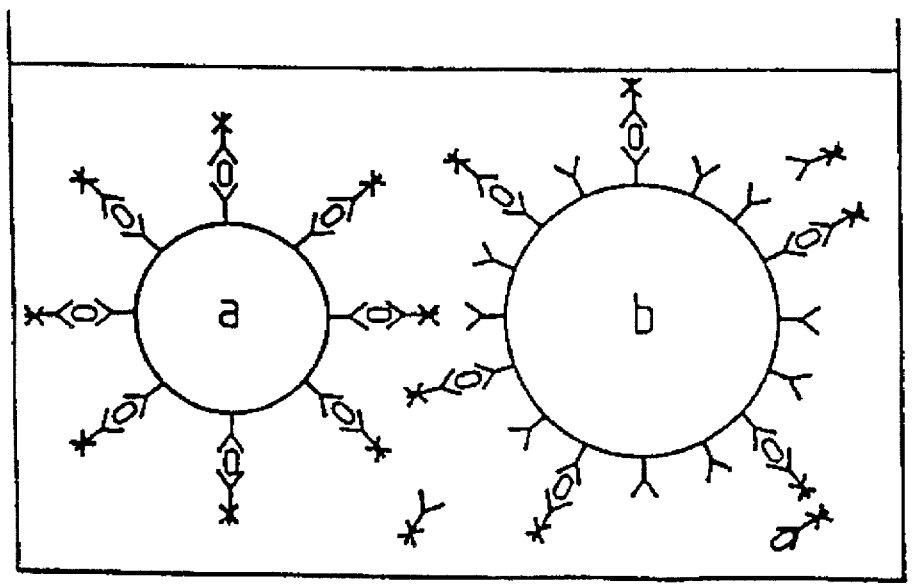
FIG. 2 depicts the binding reaction for the two types of particles in the presence of a high concentration of antigen.

When the antigen is present in high concentration (FIG. 2), the binding to type a particles will be saturated. Excess antigen will bind to the low affinity binding sites on type D particles. They are present in relatively large concentration, and saturation will therefore occur only for particularly high concentrations of the antigen.

In FIGS. 3 and 4 panel A shows histograms of the number of registered events (counts per channel, y-axis) as a function of the intensity of the light scatter signal (x-axis, Linear scale). The two types of particles a and b are seen as clearly separated populations. Panel B shows the fluorescence distribution for type a particles, i.e. the number of registered events (y-axis) as a function of fluorescence intensity per particle (x-axis, logarithmic scale). Data acquisition in this histogram has been gated on window a in the light scatter distribution of panel A, i.e. only particles registered within window a on light scatter will have their fluorescence measurement registered in the histogram of panel B. Panel B thus shows the fluorescence distribution of type a particles. In a similar way, the fluorescence distribution of type b particles has been registered in panel C. Panel D is a two-parameter plot which shows the two populations a and b according to their respective values in light scatter (y-axis, linear scale) and fluorescence (x-axis, logarithmic scale). In this case the histogram has been acquired without gating conditions. Therefore both populations a and b show up in panel D.

FIG. 3 shows relatively high fluorescence intensity for the small (type a) particles, while the fluorescence associated with the larger (type b) particles is less. This result corresponds to a relatively low antigen concentration where the antigen preferably binds to type a particles.

FIG. 4 shows corresponding data for a relatively high antigen concentration, resulting in strong fluorescence for both particle types.

From measurements, such as shown in FIGS. 3 and 4, of samples of known concentrations of the antigen in question, a double standard curve is established from measurements of both particle types in each sample. Such a curve is illustrated in FIG. 5. The x-axis shows the concentration of antigen (logarithmic scale), and the y-axis represents mean fluorescence per particle for each of the two types (logarithmic scale). In FIG. 5 there is also illustrated the way in which the present invention constitutes a method exhibiting increased dynamic measurement range ($R_{a+b}$) compared with measurements based on only type a particles ($R_a$).

In General, the concentration of antigen of an unknown sample can be determined by measuring in the flow cytometer the fluorescence intensity of type a and b particles after incubation with the sample and thereafter reading the corresponding antigen concentration from the standard curve (where antigen concentration is a function of both fluorescence intensity a and fluorescence intensity b).

Tests of this invention have been performed with Dynosphere™ monodisperse particles in the size range 1–10 um. It is an important advantage that the particles are uniform in size as well as surface area and characteristics, since this results in less variance in the amount of binding partner per particle after the coating process, and therefore gives less variance in fluorescence per particle after binding of analyte and labelled reagent. Since the flow cytometer gives results in the form of histograms of particle-associated fluorescence from populations of typically 10,000 particles, demonstration of a difference in mean binding per particle between two samples will be more precise the smaller the variance of the fluorescence distributions. In addition, uniformity in size requires less difference in mean size between the two types a and b for them to be reliably identified and separately classified by the flow cytometer.

This is of particular importance if the present invention is used to determine concentrations of more than one analyte in the same sample or to determine more than one form of a particular analyte in the same sample. This is done by using one pair of particles for each analyte specificity as explained above, but chosen such that all particle types used in the mixture can be distinguished in the flow cytometer, e.g. from their different sizes.

The present method may be used to read the results after the binding reaction has reached complete equilibrium. It should be noted that true equilibrium can only exist in homogeneous assays, since a separation step with removal of free reagents will initiate a reverse dissociation reaction. Reading by flow cytometry therefore permits measurement at true equilibrium, as opposed to methods based on separation.

In some cases it may, however, be an advantage to measure before equilibrium is reached. Thereby differences in binding kinetics between the two types of particles can be exploited. The present invention thus permits continuous measurement of particles as a function of time, since all reagents are continuously present. For such applications, flow cytometry makes it possible to start measuring only a few seconds after mixing the reagents with the sample.

Since the present invention is based on measuring two quantities for each determination instead of one, which is conventional, there is a more reliable relationship between a set of measurements and the corresponding analyte concentration. The double standard curve (FIG. 5) defines corresponding values of expected fluorescence intensities for the two particle types. If a pair of values is registered that does not correspond to a well defined point on the concentration scale in the double standard curve, this indicates an error or unknown factor in the performance of the assay, and therefore serves as a warning of an unreliable result. In a similar way, a pair of measurement values that fit well into the double standard curve will give increased reliability in determining the corresponding concentration, compared to methods based on only one measurement parameter. This provides an internal control of the reliability of the results.

The measurement in the flow cytometer has in itself an internal control in that the light scatter or similar histogram registered from the particle mixture (panel A, FIG. 3 and 4) will remain essentially the same for all samples within a series. Possible errors due to malfunctioning of the flow cytometric measurement process can therefore easily be identified.

In addition to applications for assay of unknown analyte concentrations in a sample, the present invention can be used to determine binding affinity and binding kinetics of a substance attached to one type of particle, by comparing with a substance having known binding partners coated onto a different type of particle, such determination being based on determination or assay of the amount of analyte substances binding to each of said particles in accordance with the invention.

EXAMPLE

Materials and Methods

Microsphere particles

Two different sizes of otherwise identical types of polymer particles ,were used The particles were produced according to a newly developed two-step process for preparation of relatively large (1–100 um) monodisperse particles of homogeneous characteristics (Ugelstad et al., Adv. Colloid Interface Sci 13,101, 1980). The particles used (SS-072-R of 7 um diameter and SS-102-R of 10 um diameter) are referred to as MP7 and MP10, respectively (Dyno Particles, N-2001 Lillestrom, Norway), and were made from compact styrene.

Monoclonal antibodies

Three different antibodies against carcinoembryonic antigen (CEA) were used. The two used for particle coating were crossreacting antibodies directed against the same epitope on the CEA molecule. The antibody 12-140-5 (IgG2a) used to coat the smaller MP7 particles had an association constant of $3.2 \times 10^{10} M^{-1}$, the antibody 12-140-10 (IgG1) used for the larger MP10 particles has an association constand of $3.3 \times 10^{9} M^{-1}$. The third antibody (12-140-1, IgG1) was used as labelled antibody and was directed against a different CEA epitope, thus fulfilling the requirement for a two-site immunometric assay. This antibody was conjugated to biotin essentially as described by Guesdon et al (J. Histochem. Cytochem, 27,1131 1979 using biotin-aminocaproic acid N-hydroxysuccinimide ester (Calbiochem). A ratio of 50 biotin molecules to each antibody molecule was used and the reaction was carried out in 0.1M $NaHCO_3$ at pH 9.5 for 16 h at room temperature. The labelled antibody was separated from free biotin by gel filtration through a BioGel P30 column (2.2×24 cm) in PBS. All antibody molecules contained functionally active biotin residues. All three antibodies were mouse monoclonal antibodies.

Particle coating

Physical adsorption was used to coat the particles with the primary antibodies. One mg of antibody 12-140-10 was incubated with 400 mg of MP10 particles in 5 ml of PBS during slow end-over-end rotation overnight at room temperature. The adsorption of 12-140-5 antibody was carried out using 1 mg antibody and 100 mg MP7 particles in 2.5 ml PBS. The particles were washed three times in 1% BSA-PBS-$NaN_3$. The MP7 particles bound 4.6 ug of antibody per mg of particles, the MP10 particles bound 2.0 ug/mg. Coated microspheres were stored at 4° C. prior to use, and only insignificant dissociation of antibody from the surface was observed over several months of storage.

CEA standard

A dilution series was made from purified CEA determined to contain 6750 ug/l (Bormer, Clin. Biochem, 15,128 1982).

Assay procedure

Serial 1:3 dilutions of CEA in the concentration range 0.2 ug/l to 1350 ug/l were made up in 1% BSA-PBS as 200 ul samples in Eppendorf tubes. From a reagent mixture containing one part MP7 particles (concentration $9 \times 10^6$ particles/ml), one part MP10 particles (concentration $15 \times 10^6$ particles/ml) , one part secondary biotin-labelled 12-140-1 antibody (concentration 14 ug/ml), and one part Streptavidin-Phycoerythrin Conjugate (undiluted, Becton Dickinson Immunocytometry Systems, Mountain View, Calif.), 40 ul was added to each CEA sample, resulting in a 24×dilution of the individual reagent concentrations cited above. The samples were incubated for several hours in the dark at room temperature with slow end-over-end rotation, and directly analyzed in the flow cytometer without washing.

Flow cytometric analysis

Samples were analyszed in a Coulter EPICS V flow cytometer (Coulter EPICS Division, Hialeah, Fla.) using 600 mW of the 488 nm line from an Argon ion laser for excitation of phycoerythrin fluorescence. Detection was in the region 550–590 nm. Separate histograms of logarithmic fluorescence intensity representing the two particle types MP7 and MP10 were acquired by means of gating on windows set in the light scatter histogram for each of the two populations. The mean channel number of the logarithmic fluorescence histogram was taken as a measure of the particle-associated immunofluorescence.

RESULTS

FIG. 6 shows an example of flow cytometric data recorded for a sample containing 50 ug/ml of CEA. The light scatter distribution in panel A was used to set gating windows distinguishing the two particle populations MP7 and MP10, labelled a and b, respectively. Separate histograms of logarithmic fluorescence intensity for the two populations (Panel C: MP7. Panel D: MP10) were obtained by gating the fluorescence data acquisition in the windows set in the light scatter distribution. For each fluorescence histogram the mean channel number, i.e. the mean of logarithmic fluorescence intensity, was taken as the measure of antigen binding to the particles. A two-parameter histogram of light scatter versus logarithmic fluorescence intensity (panel B) showed the total correlated data from both particle populations.

Figure 7A:
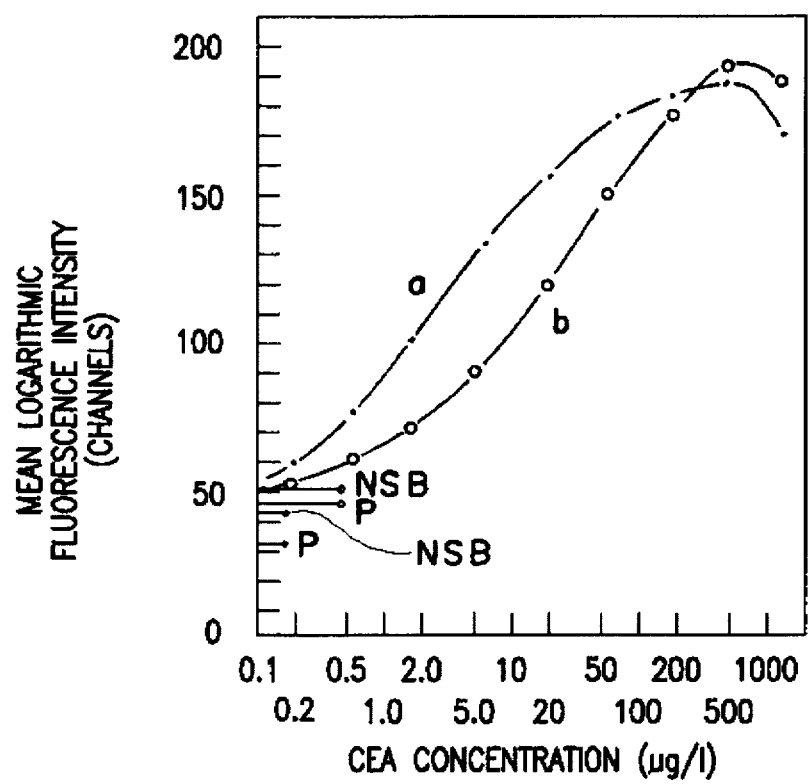

FIG. 7A shows the double standard curve obtained by plotting the mean channel number of the fluorescence distributions for MP7 (a) and MP10 (b) particles as a function of the CEA concentration of the sample. The high affinity MP7 particles (a) exhibited significant binding already at 0.2 ug/l (1 pM), whereas the binding to the MP10 low affinity particles (b) at this concentration was not significantly different from the level shown for nonspecific binding (NSB). The signal level from particles with no added reagents is also shown (P).

Throughout the low and middle range of concentrations tested, the high affinity particles had a higher fluorescence than the larger, low affinity particles. However, as the fluorescence intensity for the high affinity particles leveled off at high CEA concentration, and eventually started to decrease due to the Hook effect, the fluorescence intensity measured for the low affinity particles was still increasing with CEA concentration.

Figure 7B:
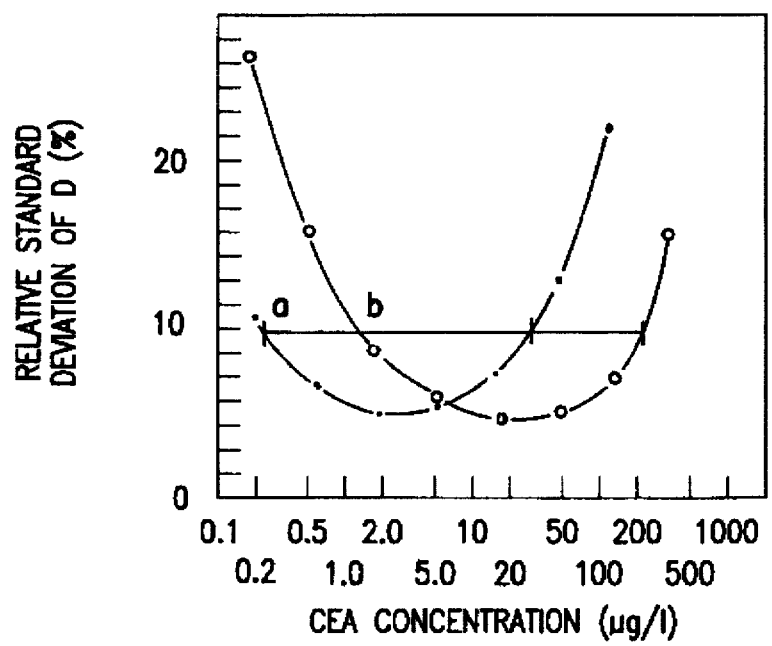

FIG. 7B shows the double precision profile for this type of assay as calculated from the data shown in FIG. 7A. The precision profile is a plot of the relative uncertainty in the determination of a certain antigen concentration or dose (D), over the range of concentrations used in the assay (Ekins, 1983 in Immunoassays for Clinical Chemistry, 2nd Edition Churchill and Livingstone, p. 76). The precision profile is usually calculated from the total set of parallel samples at different concentrations. However, the important influence of the shape of the standard curve for the precision profile can be derived from the double standard curve in FIG. 7A.

FIG. 7B shows values of the relative standard deviation of D in percent based on a difference of 2.0 in mean channel values between parallel histograms of replicate samples. The horizontal line drawn in FIG. 7B to indicate the working range of the assay corresponds to a level of 10% precision.

At this level of 10% precision, the double precision profile indicates a working range from about 0.2 to 200 ug/l, corresponding to a dynamic range of 3 decades. The measurement obtained from the high affinity particles provides high precision in the low concentration range, and the measurement from the low affinity particles provides precision in the high concentration range. As shown by FIG. 7B, the range obtained by using the high affinity particles alone would correspond to 2 decades, or probably less.

I claim:

1. In a method for the flow cytometric assay of an analyte in an aqueous sample using monodisperse particles carrying a specific binding partner therefor, said analyte and binding partner being selected from the group consisting of (a) antigen and specific antibody, (b) hormone and hormone receptor, (c) hapten and antihapten, (d) polynucleotide and polynucleotide binding protein, (e) biotin and avidin or streptavidin, and (f) lectin and specific carbohydrate, and said method comprising the steps of adding to the aqueous sample a predetermined amount of said particles and a predetermined amount of a labelled ligand having affinity for the analyte or the binding partner and detecting and quantifying the resulting labelled ligand-carrying particles by means of a flow cytometer, the improvement consisting of using a pair of a different particle types which are distinguishable from each other by the flow cytometer and which respectively carry binding partners having the same specificity but different binding affinity for the analyte and independently but simultaneously detecting and quantifying the two types of labelled ligand-carrying particles by means of the flow cytometer and determining the analyte concentration from the thus-obtained two measurement values by reference to a double standard calibration curve; said double standard calibration curve having one curve which quantitatively shows the amount of label bound to one of the pairs of particle types as a function of analyte concentration in the sample and another curve which quantitatively shows the amount of label bound to the other particle type as a function of analyte concentration in the sample.

2. A method as claimed in claim 1 in which all the monodisperse particle types used are distinguished by the flow cytometer by differences in particle size.

3. A method as claimed in claim 1 in which said label is a substance providing a photometric signal which can be determined quantitatively by the flow cytometer.

4. A method as claimed in claim 3 in which the signal is a fluorescence signal.

5. A method as claimed in claim 4 in which differences in particle size for different particle types are determined by estimating scattering of light produced by a light source also triggering the said fluorescence signal.

6. A method as claimed in claim 1 wherein flow cytometry is effected when the analyte binding reaction has reached equilibrium.

7. A method as claimed in claim 1 in which the flow cytometry is effected before the analyte binding reaction has reached equilibrium whereby the kinetics of the binding reaction may be examined.

8. A method as claimed in claim 1 in which monodisperse particles of a further particle type which carry an antibody having zero affinity for the analyte or analytes to be assayed are included, thus providing an indication of the level of non-specific binding of the labelled binding partner.

9. A method as claimed in claim 1 in which the analyte is an antigen and the binding partner therefor is a monoclonal antibody.

10. The method of claim 1 in which a plurality of analytes is simultaneously assayed using a plurality of pairs of particle types, all of said particle types being separately distinguishable from each other by the flow cytometer.

* * * * *